(12) United States Patent
Tsai et al.

(10) Patent No.: US 11,752,104 B2
(45) Date of Patent: Sep. 12, 2023

(54) ORAL COMPOSITION AND METHODS FOR MANUFACTURING THE SAME AND TREATMENT

(71) Applicant: MEDICAL AND PHARMACEUTICAL INDUSTRY TECHNOLOGY AND DEVELOPMENT CENTER, New Taipei (TW)

(72) Inventors: Meng-Kun Tsai, Taipei (TW); Chih-Chiang Yang, New Taipei (TW); Wen-Che Wang, New Taipei (TW); Tzu-Yu Chien, New Taipei (TW); Chien-Chia Wu, New Taipei (TW); Lai-Cheng Chin, New Taipei (TW)

(73) Assignee: MEDICAL AND PHARMACEUTICAL INDUSTRY TECHNOLOGY AND, New Taipei (TW)

( * ) Notice: Subject to any disclaimer, the term of this patent is extended or adjusted under 35 U.S.C. 154(b) by 0 days.

(21) Appl. No.: 16/887,259

(22) Filed: May 29, 2020

(65) Prior Publication Data
US 2020/0375901 A1 Dec. 3, 2020

Related U.S. Application Data

(60) Provisional application No. 62/854,969, filed on May 31, 2019.

(51) Int. Cl.
| | |
|---|---|
| *A61K 9/16* | (2006.01) |
| *A61K 31/717* | (2006.01) |
| *A61K 31/436* | (2006.01) |
| *A61K 9/00* | (2006.01) |

(52) U.S. Cl.
CPC ............ *A61K 9/167* (2013.01); *A61K 9/0053* (2013.01); *A61K 31/436* (2013.01); *A61K 31/717* (2013.01)

(58) Field of Classification Search
None
See application file for complete search history.

(56) References Cited

U.S. PATENT DOCUMENTS

| | | |
|---|---|---|
| 2006/0034937 A1 | 2/2006 | Patel |
| 2006/0159766 A1 | 7/2006 | Jenkins et al. |
| 2008/0152720 A1* | 6/2008 | Jenkins .................. A61P 37/00 424/494 |
| 2018/0243224 A1 | 8/2018 | Banait et al. |

FOREIGN PATENT DOCUMENTS

| | | | |
|---|---|---|---|
| CN | 101744785 | * | 6/2010 |
| CN | 101744785 A | | 6/2010 |
| CN | 106309395 A | | 1/2017 |
| CN | 103479600 B | | 1/2018 |
| CN | 107595784 A | | 1/2018 |

OTHER PUBLICATIONS

Steimer et al. Advanced Powder Technology. Breakage, Temperature Dependency and Contamination of Lactose During Ball Milling in Ethanol. June (Year: 2016).*
I Ghosh, D Schenck, S Bose, C Ruegger, Optimization of formulation and process parameters for the production of nanosuspension by wet media milling technique: Effect of Vitamin E TPGS and nanocrystal particle size on oral absorption, European Journal of Pharmaceutical Sciences, vol. 47, Issue 4 (Year: 2012).*
Peltonen, L. et al., "Pharmaceutical Nanocrystals by Nanomilling: Critical Process Parameters, Particle Fracturing and Stabilization Methods", Journal of Pharmacy and Pharmacology vol. 62, No. 11, Jul. 20, 2010, 1569-1579.
Peltonen, L. et al., "Space and QbD Approach for Production of Drug Nanocrystals by Wet Media Milling Techniques", Pharmaceutics, 10, Jul. 25, 2018.
Tuomela, A. et al., "Production, applications and in vivo fate of drug nanocrystals", Journal of Drug Delivery Science and Technology, vol. 34, Mar. 3, 2016, 21-31.
Yang, C. et al., "Recent Advances in the Application of Vitamin E TPGS for Drug Delivery", Theranostics. vol. 8, No. 2, Jan. 1, 2018, 464-485.
Quinapril Hydrochloride, CAS 82586-55-8, Santa Cruz Biotechnology, downloaded from the internet—URL: https://www.scbt.com/p/quinapril-hydrochloiide-82586-55-8, 1-5.

* cited by examiner

*Primary Examiner* — Nicole P Babson
(74) *Attorney, Agent, or Firm* — Joseph C. Zucchero; Carolyn S. Elmore; Elmore Patent Law Group, P.C.

(57) ABSTRACT

An oral composition includes an immediate-release pharmaceutical admixture and an extended-release pharmaceutical admixture. The immediate-release pharmaceutical admixture includes a first portion of an active ingredient and a first portion of a hydrophilic dispersant, in which the active ingredient is substantially insoluble in water. The extended-release pharmaceutical admixture includes a controlled-release material, a second portion of the active ingredient, and a second portion of the hydrophilic dispersant, wherein the second portion of the active ingredient and the second portion of the hydrophilic dispersant are mixed in the controlled-release material, wherein the active ingredient is present as a nanoparticle in the immediate-release pharmaceutical admixture and the extended-release pharmaceutical admixture.

16 Claims, 3 Drawing Sheets

ORAL COMPOSITION AND METHODS FOR MANUFACTURING THE SAME AND TREATMENT

CROSS-REFERENCE TO RELATED APPLICATION

This application claims priority to U.S. Provisional Application Ser. No. 62/854,969, filed May 31, 2019, which is herein incorporated by reference in its entirety.

BACKGROUND

Field of Invention

The present invention relates to a pharmaceutical composition for acquiring immediate release and extended release and a method for manufacturing the same and using the same for treatment of a symptom or a disease caused by immune response or for treatment of organ rejection.

Description of Related Art

Typically, an oral dosage form for the delivery of active ingredients releases the active ingredients during passing through the gastrointestinal tract (GI tract). Among the release process, the characteristics of active ingredients and release forms mainly contribute to the bioavailability of active ingredients. Especially, active ingredients which are substantially water insoluble, the water solubility less than 30 mg/ml and sometimes existing in solid particles with irregular shapes, lead to the less, and sometimes variable, bioavailability of active ingredients in subjects.

To improve the applicability of active ingredients which are substantially water insoluble, methods about increasing the solubility of the active ingredients or selecting the appropriate release forms, such as dissolving the active ingredients in appropriate dispersants, are considered.

One of which about increasing the solubility is reducing the particle size by milling. Nevertheless, the concern about milling for particle size reduction is that the high-energy molecule is usually converted to low-energy crystalline form, therapeutically inactive, in the milling process and agglomeration possibly forms in/after the milling process, leading to a decrease in the effective surface area for dissolution and inconvenience in storage.

For another, release forms can be generally divided into immediate release (IR) form or extended release (ER) form, formulated by the corresponding procedures and distinctive added components, according to the maximum blood plasma/media concentration of the active ingredients (Cmax). IR form releases the active ingredients rapidly, leading to a rapid rise to Cmax of active ingredients in the blood/media in a short time, usually followed by a rapid decrease in concentration as the active ingredients are cleared from the body. If the concentration of active ingredients rises and decreases rapidly, this may create a narrow window of time for maintaining therapeutic effect, thereby increasing the demanded dosage frequency. Furthermore, the rapid release of active ingredients of IR form, higher than maximum tolerance concentration, may even be harmful to subjects' health. On the other side, ER form is directed to provide sustained therapeutic efficacy. Nevertheless, ER form, characteristically at low concentration in the initial-release period, falls short of rapid onset of therapeutic effect. Thus, subjects with diseases or conditions needing immediate onset of therapeutic effect, e.g., pain releasing relief or avoid of organ rejection, are advised to be administered with other dosage form or in combination with IR form.

SUMMARY

The object of the present invention is to provide an oral composition, a method for manufacturing the same, and a method for treatment of a symptom or a disease caused by immune response or for treatment of organ rejection including administering a subject with the same.

The oral composition of the present disclosure includes: an immediate-release pharmaceutical admixture including a first portion of an active ingredient and a first portion of a hydrophilic dispersant, wherein the active ingredient is substantially insoluble in water, and an extended-release pharmaceutical admixture including a controlled-release material, a second portion of the active ingredient, and a second portion of the hydrophilic dispersant, wherein the second portion of the active ingredient and the second portion of the hydrophilic dispersant are mixed in the controlled-release material, wherein the active ingredient is present as a nanoparticle in the immediate-release pharmaceutical admixture and the extended-release pharmaceutical admixture.

In another aspect, the method for manufacturing the oral composition of the present disclosure is provided, including steps of: milling an active ingredient to form a milled active ingredient having a particle size of D90 of 100 nm to 3000 nm, mixing the milled active ingredient with a filler and a hydrophilic dispersant in liquid phase to form a liquid precursor, drying the liquid precursor to form an immediate-release pharmaceutical powder, mixing a controlled-release material with the immediate-release pharmaceutical powder to form an extended-release pharmaceutical admixture, and mixing the extended-release pharmaceutical admixture with the immediate-release pharmaceutical powder.

In another aspect, the method for treatment of a symptom or a disease caused by immune response or for treatment of organ rejection is provided, including administering a subject with the oral composition of the invention.

Particularly important to this disclosure is the use of milling technique with proper parameters and suitable materials added, avoiding inactivation of active ingredients and achieving better bioavailability, and the appropriate mixture ratio and the materials involved in oral composition, ensuring the stable and extended release of active ingredients within the prolonged period, providing the benefits of enhanced subject convenience and compliance.

It is to be understood that both the foregoing general description and the following detailed description are by examples, and are intended to provide further explanation of the invention as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
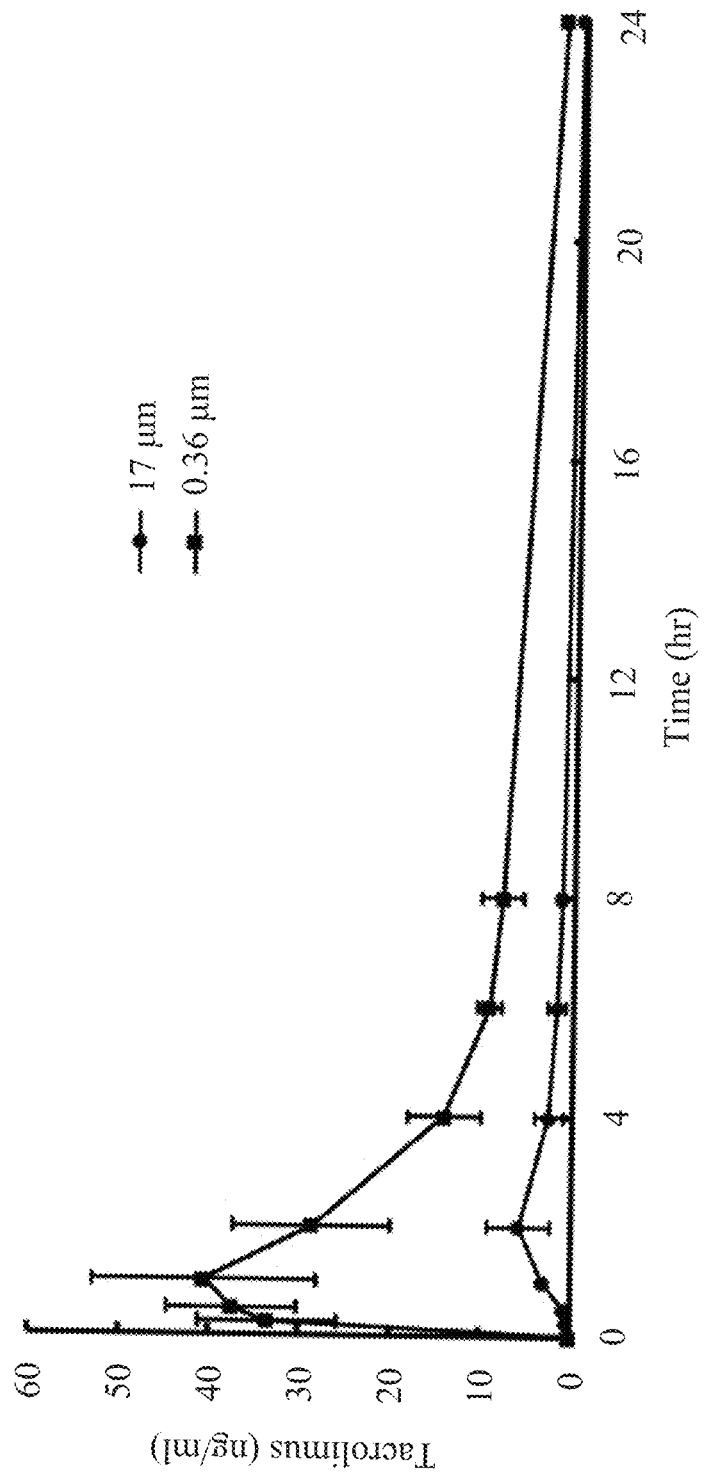
FIG. 1 shows a curve of tacrolimus blood concentration in rats while feeding with unmilled particles (D90 of 17 μm) and 90-min milled particles (D90 of 0.36 μm) according to Examples of the present disclosure.

Reference will now be made in detail to the present embodiments of the invention, examples of which are illustrated in the accompanying drawings. Wherever possible, the same reference numbers are used in the drawings and the description to refer to the same or like parts.

Definitions

As used herein, "a," "an," and "the," include their corresponding plural references unless the context clearly dictates otherwise.

As used herein, the terms "comprising," "including," "having," "containing," and the like are to be understood to be open-ended, i.e., to mean including but not limited to.

As used herein, "About" when used to modify a numerically defined parameter means that the parameter may vary by as much as 10% below or above the stated numerical value for that parameter.

As used herein, "Bioavailability" refers to a subcategory of absorption in pharmacology and is the fraction of an administered dose of intact drug that reaches the systemic circulation.

As used herein, "Immediate Release (IR)" refers to release of an active ingredient without delaying or prolonging dissolution or absorption.

As used herein, "Extended Release (ER)" refers to release of an active ingredient at a predetermined rate in order to maintain an active ingredient concentration for a specific period of time with minimum side effects.

As used herein, "substantially insoluble in water" refers to active ingredients that have a solubility in water of less than about 30 mg/ml, preferably less than about 20 mg/ml, about 10 mg/ml, about 1 mg/ml, about 500 μg/ml, about 100 μg/ml, about 50 μg/ml, about 10 μg/ml, or about 1 μg/ml.

As used herein, "nanoparticle" refers to a microscopic particle with the dimension of less than about 5000 nm.

As used herein, "Cmax" refers to the maximum blood plasma/media concentration of the active ingredients.

As used herein, "Tmax" refers to the time point at which Cmax is reached.

As used herein, "D90" refers to the particle diameter corresponding to 90% cumulative (from 0 to 100%) undersize particle size distribution.

Oral Composition

The present invention is directed to an oral composition comprising an immediate-release pharmaceutical admixture and an extended-release pharmaceutical admixture. The immediate-release pharmaceutical admixture includes a first portion of an active ingredient and a first portion of a hydrophilic dispersant, wherein the active ingredient is substantially insoluble in water. The extended-release pharmaceutical admixture includes a controlled-release material, a second portion of the active ingredient, and a second portion of the hydrophilic dispersant, wherein the second portion of the active ingredient and the second portion of the hydrophilic dispersant are mixed in the controlled-release material, wherein the active ingredient is present as a nanoparticle in the immediate-release pharmaceutical admixture and the extended-release pharmaceutical admixture.

In some embodiments of the present disclosure, the active ingredient is dispersed in the immediate-release pharmaceutical admixture and the extended-release pharmaceutical admixture.

In some embodiments of the present disclosure, the active ingredient has a particle size of D90 of 100 nm to 5000 nm, D90 of 100 nm to 4800 nm, D90 of 100 nm to 4600 nm, D90 of 100 nm to 4400 nm, D90 of 100 nm to 4200 nm, D90 of 100 nm to 4000 nm, D90 of 100 nm to 3800 nm, D90 of 100 nm to 3600 nm, D90 of 100 nm to 3400 nm, D90 of 100 nm to 3200 nm, D90 of 100 nm to 3000 nm, D90 of 100 nm to 2800 nm, D90 of 100 nm to 2600 nm, D90 of 100 nm to 2400 nm, D90 of 100 nm to 2200 nm, D90 of 100 nm to 2000 nm, D90 of 100 nm to 1800 nm, D90 of 100 nm to 1600 nm, D90 of 100 nm to 1400 nm, D90 of 100 nm to 1200 nm, D90 of 100 nm to 1000 nm, D90 of 100 nm to 800 nm, D90 of 100 nm to 600 nm, D90 of 100 nm to 400 nm, D90 of 100 nm to 200 nm. Preferably, the active ingredient has the particle size of D90 of about 200 nm to about 400 nm. Preferably, the active ingredient has the particle size of D90 of about 360 nm to about 400 nm.

In one embodiment, the immediate-release pharmaceutical admixture and the extended-release pharmaceutical admixture are separately or independently formulated in different amorphous solid dispersions. These solid dispersions are mixed, optionally other excipients being added, to form the oral composition of the present invention.

In yet another embodiment, the immediate-release pharmaceutical admixture and the extended-release pharmaceutical admixture are formulated in the same amorphous solid dispersion. The solid dispersion can be optionally mixed with other excipients. In some embodiments, the immediate-release pharmaceutical admixture and the extended-release pharmaceutical admixture are compressed into a tablet.

In another embodiment, the solid dispersion is produced by melt-extrusion, spray-drying or other techniques which can prepare the solid dispersion into any suitable solid oral dosage forms. In further another embodiment, the solid dispersion can be compressed into tablets or mini-tablets. In yet another embodiment, the solid dispersion can be either directly compressed, or milled or ground to granules or powders before compression. Compression can be done in a tablet press, such as in a steel die between two moving punches.

In still another embodiment, the immediate-release pharmaceutical admixture and the extended-release pharmaceutical admixture are formulated in the same amorphous liquid dispersion. The liquid dispersion can be optionally mixed with other excipients. In some embodiments, the liquid dispersion of the oral composition can be directly administered. In some embodiments, the liquid dispersion is manufactured to capsules.

In yet another embodiment, one of the immediate-release pharmaceutical admixture and the extended-release pharmaceutical admixture is formulated in the amorphous liquid dispersion. The liquid dispersion of immediate-release pharmaceutical admixture or the extended-release pharmaceutical admixture can be optionally mixed with other excipients and another pharmaceutical admixture, thereby manufactured to capsules.

In further another embodiment, the weight ratio of the immediate-release pharmaceutical admixture to the extended-release pharmaceutical admixture is about 2:8 to about 4:6, or preferably ranged from 2.5:7.5 to about 3.5:6.5. More preferably, the weight ratio of the immediate-release pharmaceutical admixture to the extended-release pharmaceutical admixture is about 3:7.

In some embodiments, the weight percentage of the active ingredient in oral composition is ranged from 0.01% to 0.8%. In one embodiment, the weight percentage of the active ingredient in oral composition is 0.5% to 0.8%, 0.5% to 0.7%, 0.5% to 0.6%, 0.6% to 0.8%, or 0.7% to 0.8%. In some other embodiments, the weight percentage of the active ingredient in oral composition is about 0.01-0.2%.

In another embodiment, the weight ratio of the first portion of the active ingredient to the second portion of the active ingredient is ranged from 2:8 to 4:6, or more preferably 2.5:7.5 to about 3.5:6.5.

In one embodiment, the active ingredient, substantially insoluble in water, is selected from the group consisting of an immunosuppressant, an anesthetic agent, an ACE inhibiting agent, an antithrombotic agent, an anti-allergic agent, an antibacterial agent, an antibiotic agent, an anticoagulant agent, an anticancer agent, an antidiabetic agent, an antihypertension agent, an antifungal agent, an antihypotensive agent, an antiinflammatory agent, an antimicotic agent, an antimigraine agent, an antiparkinson agent, an antirheumatic agent, an antithrombin, an antiviral agent, an beta blocking agent, a bronchospamolytic agent, a calcium antagonist, a cardiovascular agent, a cardiac glycosidic agent, a carotenoid, a cephalosporin, a contraceptive agent, a cytostatic agent, a diuretic agent, an enkephalin, a fibrinolytic agent, a growth hormone, an insulin, an interferon, a lactation inhibiting agent, a lipid-lowering agent, a lymphokine, a neurologic agent, a prostacyclin, a prostaglandin, a psycho-pharmaceutical agent, a protease inhibitor, a magnetic resonance diagnostic imaging agent, a reproductive control hormone, a sedative agent, a sex hormone, a somatostatin, a steroid hormonal agent, a vaccine, a vasodilating agent, and a vitamin.

In some embodiments, the immunosuppressant comprises tacrolimus, ciclosporin or voclosporin. The antiinflammatory agent comprises indomethacin, ketoprofe or piroxicam. The lipid-lowering drugs comprise fenofibrate, clofibrate, benzafibrate, aluminum clofibrate, gemfibrozil, simfibrate, ronifibrate, ciprofibrate, etofibrate, or clofibride.

In one embodiment, the dissolution percentage of the active ingredient is about 20% to about 40% within 1 hr, within 2 hrs, within 3 hrs, or within 4 hrs and is about 75% to about 85% within 18 hrs, within 20 hrs, or within 24 hrs when assayed in 0.005% hydroxypropyl cellulose (HPC) in pH 4.5, using a US FDA-published dissolution method.

In one embodiment, the controlled release material has a weight percentage relative to the oral composition of about 5% to about 50%. Preferably, the controlled release material has a weight percentage relative to the oral composition of about 20% to about 50%, about 20% to about 40%, about 20% to about 30%, or more preferably about 20% to about 25%.

In another embodiment, the controlled release material has a weight percentage relative to the extended-release pharmaceutical admixture of about 20% to about 60%, about 20% to about 50%, about 20% to about 40%, or more preferably about 20% to about 30%.

In still another embodiment, the controlled-release material comprises hydroxypropyl methylcellulose (HPMC) or polyethylene oxide (PEO), and HPMC is selected from the group consisting of hydroxypropyl methylcellulose k4M, hydroxypropyl methylcellulose K15M, hydroxypropyl methylcellulose K100M, and hydroxypropyl methylcellulose K100MCR.

In one embodiment, the average viscosity of the hydroxypropyl methylcellulose is more than 100 cps. For example, the average viscosity of the hydroxypropyl methylcellulose is about 100 cps to 100000 cps, such as about 100 cps to 1000 cps, about 1000 cps to 10000 cps, or about 10000 cps to 100000 cps.

In one embodiment, the hydrophilic dispersant is selected from the group consisting of a polymer and a carbohydrate having a molecular weight lower than 1000 Da. In another embodiment, the hydrophilic dispersant comprises a material selected from the group consisting of d-α-Tocopheryl polyethylene glycol 1000 succinate (VitE-TPGS), sodium dodecyl sulfate (SDS), poloxamer, and hydroxypropyl methylcellulose. In still another embodiment, the hydrophilic dispersant comprises poloxamer, selected from the group consisting of poloxamer 188, poloxamer 237, poloxamer 338, and poloxamer 407. In still another embodiment, the hydrophilic dispersant comprises hydroxypropyl methylcellulose 603.

In one embodiment, the first and second portions of the hydrophilic dispersant in total have a weight percentage relative to the oral composition of 0.001% to 0.4%, 0.005% to 0.4%, 0.01% to 0.4%, 0.02% to 0.4%, 0.03% to 0.4%, 0.04% to 0.4%, 0.05% to 0.4%, 0.1% to 0.4%, 0.001% to 0.05%, 0.005% to 0.05%, 0.01% to 0.05%, 0.02% to 0.05%, or more preferably 0.03% to 0.05%. In some embodiments, VitE-TPGS has a weight percentage relative to the oral composition of 0.001% to 0.4%. In some embodiments, SDS has a weight percentage relative to the oral composition of 0.03% to 0.05%.

In one embodiment, the immediate-release pharmaceutical admixture further comprises a first portion of a filler, and the extended-release pharmaceutical admixture further comprises a second portion of the filler. In another embodiment, the filler comprises saccharides, saccharide derivatives, protein or a combination thereof. In still another embodiment, the filler comprises starch, lactose or a combination thereof. More preferably, the filler comprises potato starch or corn starch. More preferably, the filler comprises Lactose 200 mesh.

In one embodiment, the oral composition further comprises an antioxidant. In another embodiment, the antioxidant comprises a tocopherol, a phospholipid, an ascorbic acid, a phytic acid, a phenolic acid, butylated hydroxyanisole (BHA), butylated hydroxytoluene (BHT), propyl gallate (PG), tertiary butyl hydroquinone (TBHQ), sodium bisulfite, a caffeic acid, or a combination thereof. In some embodiments, the weight percentage of BHT relative to the oral composition is about 0.00005% to 0.0001%.

In one embodiment, the oral composition further comprises other excipients. The excipients including binders, lubricants, disintegrants, stabilizers or plasticizers can be added while compressing the solid dispersion. Preferably, the excipients comprise silicon dioxide or magnesium stearate. In some embodiments, these excipients can be mixed with milled pharmaceutical admixture to form the oral composition before compacting.

In one embodiment, the oral composition form is formulated into, but is not limited to, capsules, tablets, pills, powders, granules, potion, and syrup.

Method for Manufacturing the Oral Composition

In another aspect, the present invention further provides a method for manufacturing the oral composition, including steps of: milling an active ingredient to form a milled active ingredient having a particle size of D90 of 100 nm to 800 nm; mixing the active ingredient with a filler and a hydrophilic dispersant in liquid phase to form a liquid precursor; drying the liquid precursor to form an immediate-release pharmaceutical powder; mixing a controlled-release material with the immediate-release pharmaceutical powder to form an extended-release pharmaceutical admixture; and mixing the extended-release pharmaceutical admixture with the immediate-release pharmaceutical powder.

In one embodiment, the milling methods include ball milling, media milling, or homogenization. Ball milling is a low energy milling process that uses milling media, active ingredient, stabilizer, and liquid. The materials are placed in a milling vessel that is rotated at speed such that the media cascades and reduces the particle size by impaction. Media milling is a high energy milling process. Active ingredient, stabilizer, and liquid are placed in a reservoir and recirculated in a chamber containing media and a rotating shaft/impeller. Homogenization is a technique that does not use milling media. Active ingredient, stabilizer, and liquid (or active ingredient and liquid with the stabilizer added after particle size reduction) constitute a process stream propelled into a process zone. The reactant to be treated is inducted into the pump, and then forced out. The geometry of the interaction chamber produces powerful forces of sheer, impact, and cavitation which are responsible for particle size reduction.

In one embodiment, milling the active ingredient comprises an operation of controlling a temperature of the active ingredient at a temperature of 4° C. to 18° C. For example, a cold water bath or a circulation of coolant may be employed to remove the energy produced in the milling process. More preferably, a hydrophilic dispersant may be added in the active ingredient to prevent the active ingredients from aggregation during the milling process. More preferably, beads are added while milling the active ingredient for mixing homogeneously.

Method for Treatment

In another aspect, the invention provides a method for treatment of a symptom or a disease caused by immune response or for treatment of organ rejection comprising administering a subject with the oral composition of the present disclosure.

In one embodiment, the symptom or disease caused by the immune response is selected from the group consisting of autoimmune diseases, inflammatory response, dermatological diseases, and pain.

In one embodiment, the active ingredient in the oral composition comprises tacrolimus.

It will be understood that the specific dose level for any particular subject will depend upon a variety of factors: the type and degree of the cellular or physiological response to be achieved; activity of the specific active ingredient or composition employed; the age, body weight, general health, sex, and diet of the subject; the time of administration, route of administration, dissolution of the active ingredient; the duration of the treatment; active ingredients used in combination or coincidental with the oral composition; and like factors well known in the medical arts.

In one embodiment, the oral composition is administered orally at a dose of 0.25 g to 2 g per day, or preferably at a dose of about 0.5 g to 1 g per day. More preferably, the oral composition comprising tacrolimus of the disclosure is administered orally at a dose of 0.5 g in relative to commercial tacrolimus products administered at a dose of 1 g per day.

In one embodiment, the oral composition is administered once a day. One skilled in art can execute the dosing regimen according to chronotherapeutic effect, the physiological response in subjects influenced by circadian rhythm.

In one embodiment, the oral composition of the present disclosure is co-administered with therapeutically effective amount of immunosuppressive drug, antibiotics, antivirals, nonsteroidal anti-inflammatory agents, lipid-lowering agents, or antimetabolites.

It should be understood that the above-described embodiments and the following examples are given by way of illustration, not limitation. Various changes and modifications within the scope of the present invention will become apparent to those skilled in the art from the present description.

Example 1

Bioavailability of Particles Processed with Milling

Tacrolimus is known for capable of prolonging survival of a host and transplanted graft in animal transplant organs. In view of the contribution to immunosuppression, it has been developed into several kinds of pharmaceutical formulations, e.g., immediate release (IR) and extended release (ER), in the commercial market.

As it is substantially insoluble in water, problems about the poor and variable bioavailability remain in all formulation of tacrolimus. Moreover, IR formulation of tacrolimus, e.g., Prograf, has been reported the acute release of tacrolimus with higher Cmax than maximum tolerated concentration triggers adverse effects, affecting the health of patients and the grafts. In addition, ER formulation of tacrolimus, e.g., Envarsus, with the much longer Tmax contributes to the higher risk of organ rejection.

For administering active ingredients which are substantially insoluble in water, such as tacrolimus, with higher and steady bioavailability, milling technique was conducted and described below.

The particle size of tacrolimus was mechanically reduced by milling in a water solution with the addition of d-α-Tocopheryl polyethylene glycol 1000 succinate (VitE-TPGS) and hydroxypropyl methylcellulose 603 (HPMC 603) to the reaction. The milling process is conducted under the water bath at the temperature of about 4 to 18° C. for decreasing high-released energy in case of the deactivation of the milled particles.

Table 1 illustrates the statistically analyzed diameter size of the milled particles after different milling time, detected by laser particle size analyzer, Malven 3000. After milling for 90 mins, the D90 of the particles is decreased to a level of less than 400 nm. Furthermore, it was observed that preferred D90 of milled particles would be limited in the range of 100 nm to 800 nm. If D90 is less than 100 nm, the issue of particle aggregation cannot be prevented. If D90 is greater than 800 nm, the favorable effect is not significant.

TABLE 1

| Milling time | Malvern 3000 (μm) | | | | |
| --- | --- | --- | --- | --- | --- |
| (min) | D [3, 3] | D [4, 3] | D10 | D50 | D90 |
| 0 | 4.860 | 8.880 | 2.300 | 6.600 | 17.000 |
| 15 | 0.294 | 0.578 | 0.157 | 0.338 | 0.967 |
| 30 | 0.219 | 0.328 | 0.119 | 0.255 | 0.572 |
| 45 | 0.230 | 1.360 | 0.123 | 0.270 | 0.608 |
| 60 | 0.170 | 0.232 | 0.094 | 0.198 | 0.426 |
| 75 | 0.158 | 0.216 | 0.088 | 0.183 | 0.390 |
| 90 | 0.149 | 0.202 | 0.083 | 0.174 | 0.364 |

Next, the media containing 90 min-milled particles with D90 of 0.36 μm conducted in Example 1 and the media containing unmilled particles with D90 of 17.0 μm were respectively prepared to feed a group of rats including ten male Sprague Dawley (SD) rats with a weight from 270 g to 285 g via oral administration, and the blood concentration of tacrolimus of each rat was detected at the time points of pre-dose, 0.25, 0.5, 1, 2, 4, 6, 8 and 24 h post dosing. The method of detecting blood concentration of tacrolimus of each rat includes the steps of collecting 0.25 mL of the blood samples of the rats by tail vein, adding the blood samples into 10 mL anticoagulant tube containing heparin, transferring the blood samples mixed with heparin to a clean microcentrifuge tube for storage at −80° C. or further detection of the blood concentration of tacrolimus of the rats. FIG. 1 shows the tacrolimus blood concentrations in the two groups of rats, feeding with unmilled particles (D90 of 17.0 μm) and 90-min milled particles (D90 of 0.36 μm). The results show that the 90-min milled particles established increased bioavailability than the unmilled particles.

Example 2

Preparation of IR Formulation and ER Formulation

To obtain IR formulation, the 90-min milled tacrolimus particles was formulated with the components listed in Table 2. First, the particles were ground together with hydrophilic dispersant including VitE-TPGS and HPMC 603 and mixed for 5 mins below 20° C. to form powder mixture. After that, lactose and starch were sprayed in solution containing the powder mixture to form a liquid precursor, followed by drying and sieving.

| | IR admixture | |
|---|---|---|
| No. | Component | Quantity/tablet (mg) |
| 1 | Tacrolimus | 1 |
| 2 | HPMC 603 | 0.2 |
| 3 | VitE-TPGS | 0.05 |
| 4 | Lactose 200 monohydrate | 84.5 |
| 5 | Potato starch | 21 |
| 6 | Water | quantum satis (q.s.) |

To acquire extended-release (ER) admixture, the immediate-release (IR) pharmaceutical powder was mixed with the controlled-release material including HPMC K 100 LV and HPMC K 100 premium and excipients including silicon dioxide and magnesium stearate, followed by punching and polishing. The addition of the controlled-release material and the excipients can be simultaneous or in a sequential order. The added components in the preparation are listed in Table 3 below.

TABLE 3

| | ER admixture | | |
|---|---|---|---|
| No. | Component | | Quantity/tablet (mg) |
| 1 | Tacrolimus | Added in IR preparation | 1 |
| 2 | HPMC 603 | | 0.2 |
| 3 | VitE-TPGS | | 0.05 |
| 4 | Water | | q.s. |
| 5 | Potato starch | | 21 |
| 6 | Lactose 200 monohydrate | | 84.5 |
| 7 | HPMC K100 LV | Added in ER preparation | 10.5 |
| 8 | HPMC K100 premium | | 31.5 |
| 9 | Silicon dioxide | | 0.65 |
| 10 | Magnesium stearate | | 0.6 |

According to pharmacokinetics of tacrolimus, to obtain the oral composition containing IR and ER formulations, enabling to maintain the blood concentration of tacrolimus of about 6 ng/ml to about 12 ng/ml, IR admixture and ER admixture are mixed together in a weight ratio of about 3:7 to achieve the total theoretical weight of active pharmaceutical ingredients (API) of 1 mg. For reference, the added components in the preparation are listed in Table 4.

TABLE 4

| | (30:70) IR admixture:ER admixture | |
|---|---|---|
| No. | Component | Quantity/tablet (mg) |
| | IR admixture | |
| 1 | Tacrolimus | 0.3 |
| 2 | HPMC 603 | 0.06 |
| 3 | VitE-TPGS | 0.015 |
| 4 | Lactose 200 monohydrate | 25.35 |
| 5 | Potato starch | 6.3 |
| 6 | Water | q.s. |
| | ER admixture | |
| 5 | Tacrolimus | 0.7 |
| 6 | HPMC 603 | 0.14 |
| 7 | VitE-TPGS | 0.035 |
| 8 | Water | q.s. |
| 9 | Potato starch | 14.7 |
| 10 | Lactose 200 monohydrate | 59.15 |
| 11 | HPMC K100 LV | 7.35 |
| 12 | HPMC K100 premium | 22.05 |
| 13 | Silicon dioxide | 0.455 |
| 14 | Magnesium stearate | 0.42 |

Example 3

Bioavailability of the Composition Containing IR Formulation and ER Formulation

To detect the bioavailability of ER admixture with reduced particle size of tacrolimus, the dissolution assay was carried out and the procedure of which is outlined below.

Figure 2:
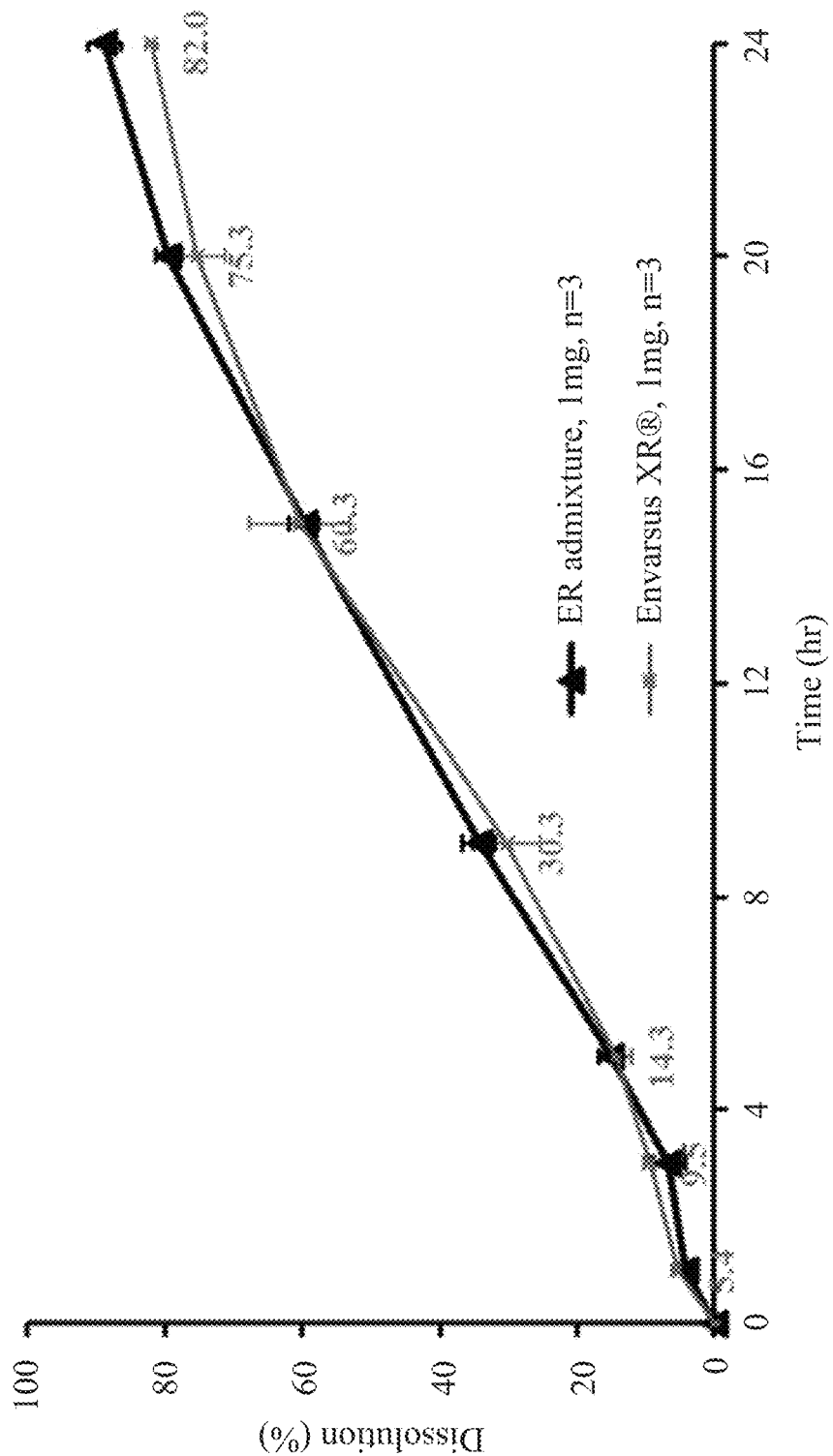
FIG. 2 is the release profiles of extended release (ER) admixture of the present disclosure and commercial Envarsus according to Examples of the present disclosure.

The release profiles of tacrolimus of ER admixture of this disclosure and commercial Envarsus, at the same dose of 1 mg, were conducted in the release medium containing 0.005% hydroxypropyl cellulose (HPC) solution, pH 4.5, at 37±0.5° C., according to the paddle method recorded in USP 42—published by the United States Pharmacopeial Convention, with three replicated experiments, depicted in FIG. 2. The ER admixture containing reduced particle size of tacrolimus demonstrated the similar dissolution profile to the commercial ER formulation of tacrolimus, Envarsus.

Figure 3:
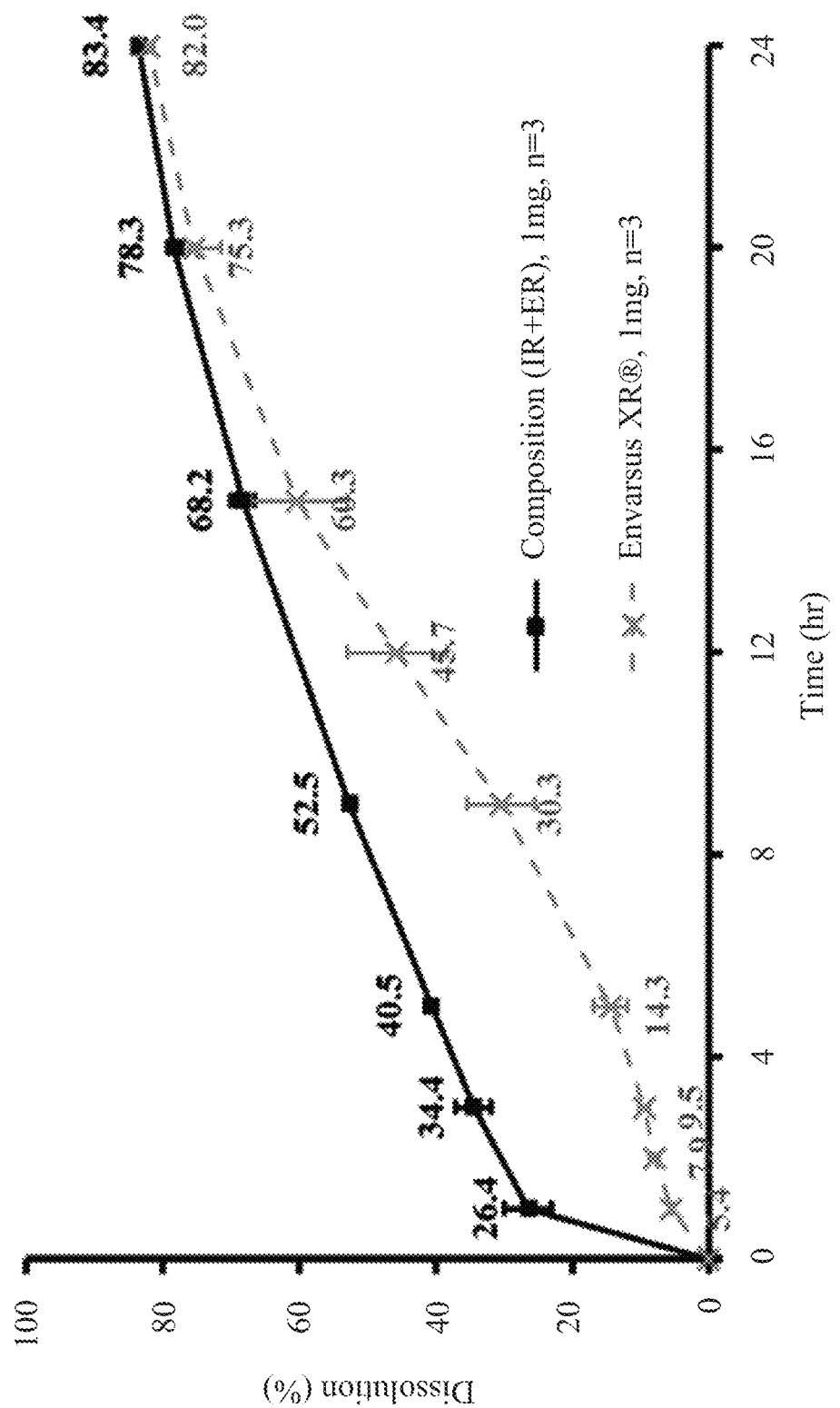
FIG. 3 is the release profiles of oral composition containing admixtures of immediate Release (IR) and ER of the present disclosure and commercial Envarsus according to Examples of the present disclosure.

In addition, the release profiles of tacrolimus of the oral composition containing both IR and ER formulations with the hardness of 78N and the dose of 1 mg were carried out in accordance with the abovementioned paddle method recorded in USP 42, in which the paddle rotation speed was 50 rpm and the release experiment was conducted in the release medium containing 0.005% hydroxypropyl cellulose (HPC) solution, pH 4.5, at 37±0.5° C., with three replicated experiments. FIG. 3 shows the release profiles of the oral composition containing both IR and ER formulations, compared with that of commercial Envarsus. For Envarsus, it needed about 4 hours to reach 10% dissolution. In contrast, the oral composition (Composition (IR+ER) in FIG. 3) established immediate release with the dissolution of up to higher than 20% in the beginning 2 hours and showed extended release with the dissolution of 70-80% within 24 hrs.

The above studies show the oral composition of the present invention has a number of enhanced pharmacological characteristics, and one skilled in the art will understand the merits of the present invention include, but are not limited to the following points, described below.

1. Increased Bioavailability & Lower Dose

The active ingredient of the oral composition, substantially insoluble in water, exhibits higher and extended bioavailability, and therefore merely a lower dose is needed in the oral composition, as compared with commercial formulations.

2. Combined Benefits of IR and ER

The oral composition overcomes the potential risks of IR, such as overdosing and toxicity in view of variable bioavailability, and the shortage of ER, such as low dissolution at the initial, leading to inability to alleviate the acute symptoms (for example, organ rejection).

3. Increased Clinical Compliance

The oral composition of the present invention with higher bioavailability, and extended-time release achieves reduced dose and lower administration frequency, thereby reducing the resistance of patients for administration and increasing clinical compliance.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the present invention without departing from the scope or spirit of the invention. In view of the foregoing, it is intended that the present invention cover modifications and variations of this invention provided they fall within the scope of the following claims.

What is claimed is:

1. A method for manufacturing an oral composition comprising
    milling a first portion of an active ingredient in a water solution with an addition of a first portion of a hydrophilic dispersant comprising d-α-Tocopheryl polyethylene glycol 1000 succinate to form a first portion of a milled active ingredient having a particle size of D90 of 100 nm to 3000 nm;
    mixing the first portion of the milled active ingredient with a filler and the first portion of the hydrophilic dispersant in liquid phase to form a liquid precursor;
    drying the liquid precursor to form an immediate-release pharmaceutical powder;
    milling a second portion of the active ingredient in the water solution with the addition of a second portion of the hydrophilic dispersant comprising d-α-Tocopheryl polyethylene glycol 1000 succinate to form a second portion of the milled active ingredient having the particle size of D90 of 100 nm to 3000 nm;
    mixing the second portion of the milled active ingredient with the filler and the second portion of the hydrophilic dispersant in liquid phase to form a liquid mixture;
    drying the liquid mixture to form an extended-release pharmaceutical pre-admixture;
    mixing a controlled-release material with the extended-release pharmaceutical pre-admixture to form an extended-release pharmaceutical admixture; and
    mixing the extended-release pharmaceutical admixture with the immediate-release pharmaceutical powder, wherein a weight ratio of the milled active ingredient of the immediate-release pharmaceutical powder to the extended-release pharmaceutical admixture is 2:8 to 4:6,
    wherein an immediate-release pharmaceutical admixture comprises the first portion of the milled active ingredient and the first portion of the hydrophilic dispersant, wherein the active ingredient is substantially insoluble in water; and
    the extended-release pharmaceutical admixture comprises the controlled-release material, the second portion of the milled active ingredient, and the second portion of the hydrophilic dispersant, wherein the second portion of the milled active ingredient and the second portion of the hydrophilic dispersant are mixed in the controlled-release material,
    wherein the milled active ingredient is present as a nanoparticle in the immediate-release pharmaceutical admixture and the extended-release pharmaceutical admixture, and
    wherein the milled active ingredient comprises tacrolimus, a dissolution percentage of tacrolimus is about 20% to about 40% within 4 hrs when assayed in 0.005% hydroxypropyl cellulose (HPC) medium in pH 4.5, and the dissolution percentage of tacrolimus is about 75% to 85% within 24 hrs when assayed in 0.005% hydroxypropyl cellulose (HPC) medium in pH 4.5.

2. The method of claim 1, wherein milling the first portion of the active ingredient comprises providing controlling a temperature of the first portion of the active ingredient at 4° C. to 18° C.

3. The method of claim 1, wherein the first and the second portions of the milled active ingredient in total have a weight percentage of 0.01% to 0.8% based on the oral composition.

4. The method of claim 1, wherein the controlled-release material has a weight percentage of 20% to 50% based on the oral composition.

5. A method for manufacturing an oral composition comprising
    milling a first portion of an active ingredient in a water solution with an addition of a first portion of a hydrophilic dispersant comprising d-α-Tocopheryl polyethylene glycol 1000 succinate to form a first portion of a milled active ingredient having a particle size of D90 of 100 nm to 3000 nm;
    mixing the first portion of the milled active ingredient with a filler and the first portion of the hydrophilic dispersant in liquid phase to form a liquid precursor;
    drying the liquid precursor to form an immediate-release pharmaceutical powder;
    milling a second portion of the active ingredient in the water solution with the addition of a second portion of the hydrophilic dispersant comprising d-α-Tocopheryl polyethylene glycol 1000 succinate to form a second portion of the milled active ingredient having the particle size of D90 of 100 nm to 3000 nm;
    mixing the second portion of the milled active ingredient with the filler and the second portion of the hydrophilic dispersant in liquid phase to form a liquid mixture;
    drying the liquid mixture to form an extended-release pharmaceutical pre-admixture;
    mixing a controlled-release material with the extended-release pharmaceutical pre-admixture to form an extended-release pharmaceutical admixture; and
    mixing the extended-release pharmaceutical admixture with the immediate-release pharmaceutical powder, wherein a weight ratio of the milled active ingredient of the immediate-release pharmaceutical powder to the extended-release pharmaceutical admixture is 2:8 to 4:6, wherein an immediate-release pharmaceutical admixture comprises the first portion of the milled active ingredient and the first portion of the hydrophilic dispersant, wherein the active ingredient is substantially insoluble in water; and the extended-release pharmaceutical admixture comprises the controlled-release material, the second portion of the milled active ingredient, and the second portion of the hydrophilic dispersant, wherein the second portion of the milled active ingredient and the second portion of the hydrophilic dispersant are mixed in the controlled-release material, wherein the milled active ingredient is present as a nanoparticle in the immediate-release pharmaceutical admixture and the extended-release pharmaceutical admixture, wherein the milled active ingredient comprises tacrolimus, and a dissolution percentage of tacrolimus is about 20% to about 40% within 4 hrs when assayed in 0.005% hydroxypropyl cellulose (HPC) medium in pH 4.5, and the dissolution percentage of tacrolimus is about 75% to 85% within 24 hrs when assayed in 0.005% hydroxypropyl cellulose (HPC) medium in pH 4.5, and wherein a blood concentration of tacrolimus is 6 ng/ml to 12 ng/ml when the oral composition is administrated to rats.

6. The method of claim 5, wherein milling the first portion of the active ingredient comprises providing controlling a temperature of the first portion of the active ingredient at 4° C. to 18° C.

7. The method of claim 5, wherein the first and the second portions of the milled active ingredient in total have a weight percentage of 0.01% to 0.8% based on the oral composition.

8. The method of claim 5, wherein the controlled-release material has a weight percentage of 20% to 50% based on the oral composition.

9. A method for manufacturing an oral composition comprising milling a first portion of an active ingredient in a water solution with an addition of a first portion of a hydrophilic dispersant comprising d-α-Tocopheryl polyethylene glycol 1000 succinate to form a first portion of a milled active ingredient having a particle size of D90 of 100 nm to 3000 nm;

mixing the first portion of the milled active ingredient with a filler and the first portion of the hydrophilic dispersant in liquid phase to form a liquid precursor;

drying the liquid precursor to form an immediate-release pharmaceutical powder;

milling a second portion of the active ingredient in the water solution with the addition of a second portion of the hydrophilic dispersant comprising d-α-Tocopheryl polyethylene glycol 1000 succinate to form a second portion of the milled active ingredient having the particle size of D90 of 100 nm to 3000 nm;

mixing the second portion of the milled active ingredient with the filler and the second portion of the hydrophilic dispersant in liquid phase to form a liquid mixture;

drying the liquid mixture to form an extended-release pharmaceutical pre-admixture;

mixing a controlled-release material with the extended-release pharmaceutical pre-admixture to form an extended-release pharmaceutical admixture; and mixing the extended-release pharmaceutical admixture with the immediate-release pharmaceutical powder, wherein a weight ratio of the milled active ingredient of the immediate-release pharmaceutical powder to the extended-release pharmaceutical admixture is 2:8 to 4:6, and the first and the second portions of the milled active ingredient in total have a weight percentage of 0.01% to 0.8% based on the oral composition;

wherein an immediate-release pharmaceutical admixture comprises the first portion of the milled active ingredient and the first portion of the hydrophilic dispersant, wherein the active ingredient is substantially insoluble in water; and the extended-release pharmaceutical admixture comprises the controlled-release material, the second portion of the milled active ingredient, and the second portion of the hydrophilic dispersant, wherein the second portion of the milled active ingredient and the second portion of the hydrophilic dispersant are mixed in the controlled-release material, wherein the milled active ingredient is present as a nanoparticle in the immediate-release pharmaceutical admixture and the extended-release pharmaceutical admixture.

10. The method of claim 9, wherein milling the first portion of the active ingredient comprises providing controlling a temperature of the first portion of the active ingredient at 4° C. to 18° C.

11. The method of claim 9, wherein the milled active ingredient comprises tacrolimus, a dissolution percentage of tacrolimus is about 20% to about 40% within 4 hrs when assayed in 0.005% hydroxypropyl cellulose (HPC) medium in pH 4.5, and the dissolution percentage of tacrolimus is about 75% to 85% within 24 hrs when assayed in 0.005% hydroxypropyl cellulose (HPC) medium in pH 4.5.

12. The method of claim 9, wherein the controlled-release material has a weight percentage of 20% to 50% based on the oral composition.

13. A method for manufacturing an oral composition comprising milling a first portion of an active ingredient in a water solution with an addition of a first portion of a hydrophilic dispersant comprising d-α-Tocopheryl polyethylene glycol 1000 succinate to form a first portion of a milled active ingredient having a particle size of D90 of 100 nm to 3000 nm;

mixing the first portion of the milled active ingredient with a filler and the first portion of the hydrophilic dispersant in liquid phase to form a liquid precursor;

drying the liquid precursor to form an immediate-release pharmaceutical powder;

milling a second portion of the active ingredient in the water solution with the addition of a second portion of the hydrophilic dispersant comprising d-α-Tocopheryl polyethylene glycol 1000 succinate to form a second portion of the milled active ingredient having the particle size of D90 of 100 nm to 3000 nm;

mixing the second portion of the milled active ingredient with the filler and the second portion of the hydrophilic dispersant in liquid phase to form a liquid mixture;

drying the liquid mixture to form an extended-release pharmaceutical pre-admixture;

mixing a controlled-release material with the extended-release pharmaceutical pre-admixture to form an extended-release pharmaceutical admixture; and mixing the extended-release pharmaceutical admixture with the immediate-release pharmaceutical powder, wherein a weight ratio of the milled active ingredient of the immediate-release pharmaceutical powder to the extended-release pharmaceutical admixture is 2:8 to 4:6, and the controlled-release material has a weight percentage of 20% to 50% based on the oral composition;

wherein an immediate-release pharmaceutical admixture comprises the first portion of the milled active ingredient and the first portion of the hydrophilic dispersant, wherein the active ingredient is substantially insoluble in water; and the extended-release pharmaceutical admixture comprises the controlled-release material, the second portion of the milled active ingredient, and the second portion of the hydrophilic dispersant, wherein the second portion of the milled active ingredient and the second portion of the hydrophilic dispersant are mixed in the controlled-release material, wherein the milled active ingredient is present as a nanoparticle in the immediate-release pharmaceutical admixture and the extended-release pharmaceutical admixture.

14. The method of claim 13, wherein milling the first portion of the active ingredient comprises providing controlling a temperature of the first portion of the active ingredient at 4° C. to 18° C.

15. The method of claim 13, wherein the first and the second portions of the milled active ingredient in total have a weight percentage of 0.01% to 0.8% based on the oral composition.

16. The method of claim 13, wherein the milled active ingredient comprises tacrolimus, a dissolution percentage of tacrolimus is about 20% to about 40% within 4 hrs when assayed in 0.005% hydroxypropyl cellulose (HPC) medium in pH 4.5, and the dissolution percentage of tacrolimus is about 75% to 85% within 24 hrs when assayed in 0.005% hydroxypropyl cellulose (HPC) medium in pH 4.5.

* * * * *